(12) United States Patent
Shan et al.

(10) Patent No.: US 9,371,394 B2
(45) Date of Patent: Jun. 21, 2016

(54) MONOCLONAL ANTIBODIES AND DETECTION METHODS FOR PHOSPHINOTHRICIN-N-ACETYL-TRANSFERASE ENZYME

(71) Applicant: DOW AGROSCIENCES LLC, Indianapolis, IN (US)

(72) Inventors: Guomin Shan, Carmel, IN (US); Eric H. Ma, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 193 days.

(21) Appl. No.: 14/049,855

(22) Filed: Oct. 9, 2013

(65) Prior Publication Data

US 2014/0099650 A1    Apr. 10, 2014

Related U.S. Application Data

(60) Provisional application No. 61/711,950, filed on Oct. 10, 2012.

(51) Int. Cl.

| | |
|---|---|
| *C07K 16/40* | (2006.01) |
| *C07K 16/12* | (2006.01) |
| *C07K 16/16* | (2006.01) |
| *C12N 5/20* | (2006.01) |
| *G01N 33/543* | (2006.01) |
| *G01N 33/569* | (2006.01) |
| *G01N 33/573* | (2006.01) |
| *C12N 5/16* | (2006.01) |

(52) U.S. Cl.
CPC .............. *C07K 16/40* (2013.01); *C07K 16/1292* (2013.01); *C12N 5/163* (2013.01); *G01N 33/543* (2013.01); *G01N 33/56961* (2013.01); *G01N 33/573* (2013.01); *C07K 16/16* (2013.01); *G01N 2333/36* (2013.01); *G01N 2333/415* (2013.01); *G01N 2333/91057* (2013.01)

(58) Field of Classification Search
CPC .... C07K 16/40; C07K 16/1292; C07K 16/16; C12N 5/163; G01N 33/543; G01N 33/56961; G01N 33/573; G01N 2333/36; G01N 2333/415; G01N 2333/91057
See application file for complete search history.

(56) References Cited

U.S. PATENT DOCUMENTS

| | | |
|---|---|---|
| 6,395,966 B1 | 5/2002 | Mumm et al. |
| 2002/0132271 A1 | 9/2002 | Onisk et al. |

FOREIGN PATENT DOCUMENTS

| | | |
|---|---|---|
| WO | 0198523 | 12/2001 |

OTHER PUBLICATIONS

Xu et al. "Application of immunoaffinity column as cleanup tool for an enzyme linked immunosorbent assay of phosphinothricin-N-acetyltransferase detection in genetically modified maize and rape," Journal of Agricultural and Food Chemistry, Jun. 1, 2005, pp. 4315-4321, vol. 53, No. 11.

Bauer-Weston, et al., "Determination of Phosphinothricin Acetyltransferase in Genetically transformed canola seed by a two-antibody sandwich enzyme immunoassay," Plant Molecular Biology Reporter, 1996, p. 134-142, vol. 14, No. 2.

International Search Report and Written Opinion for PCT Application No. PCT/US2013/064103, dated Janaury 27, 2014.

*Primary Examiner* — Gail R Gabel
*Assistant Examiner* — James L Grun
(74) *Attorney, Agent, or Firm* — Ronald S. Maciak; Magleby Cataxinos & Greenwood

(57) ABSTRACT

Described herein are monoclonal antibodies and methods useful for determining and quantitating the presence of a phosphinothricin-N-acetyl-transferase enzyme. The claimed antibodies and methods are particularly useful for identifying and quantitating the presence of phosphinothricin-N-acetyl-transferase expressed in trangenic plants.

17 Claims, 1 Drawing Sheet

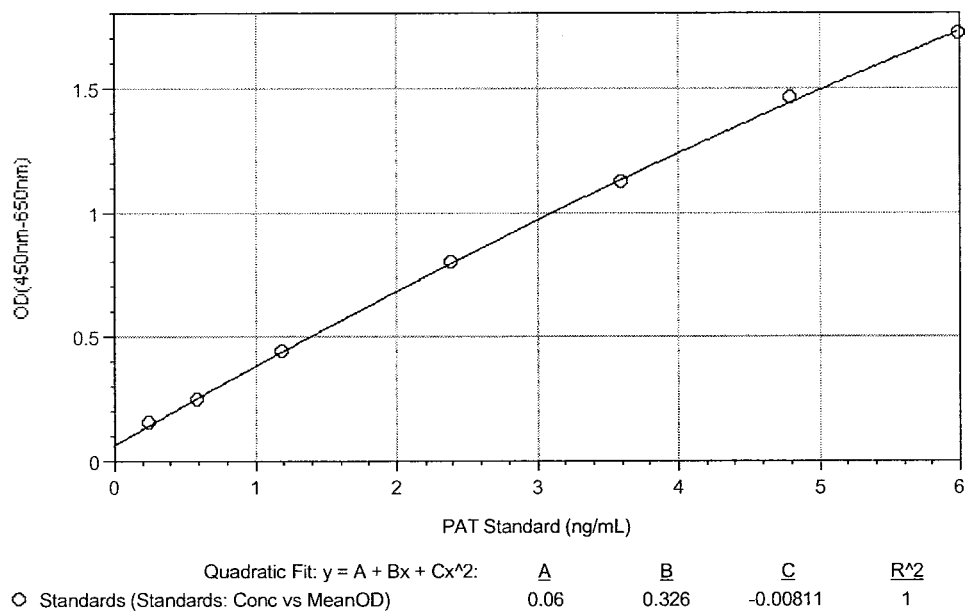

MONOCLONAL ANTIBODIES AND DETECTION METHODS FOR PHOSPHINOTHRICIN-N-ACETYL-TRANSFERASE ENZYME

CROSS-REFERENCE TO RELATED APPLICATION

This application claims the benefit of U.S. Patent Application Ser. No. 61/711,950, filed Oct. 10, 2012, the disclosure of which is hereby incorporated herein in its entirety by this reference.

TECHNICAL FIELD

This invention relates to the field of immunology as applied to ELISAs (enzyme linked immunosorbent assays) designed to detect enzymes expressed by certain transgenic plant events that confer resistance to glufosinate, L-phosphinothricin, herbicides.

BACKGROUND

Genes encoding phosphinothricin-N-acetyl-transferase (PAT), EC 2.3.1.183, are routinely used as selectable markers in transgenic events in plants and were originally isolated from the common aerobic soil actinomycete, *Streptomyces viridochromogenes*. The PAT enzyme catalyzes the acetylation of phosphinothricin, detoxifying it into an inactive compound resulting in the accumulation of ammonia and cell death (Murakami T., Anzai H., Imai S., Satoh A., Nagaoka K., Thompson C. J. (1986). *Mol Gen Genet* 205:42-50; Twell D., Klein T. M., Fromm M. E., McCormick S. (1989). *Plant Physiol* 91:1270-1274.). Transformed plant cells expressing PAT can therefore be selected using glufosinate.

Companies who develop and market recombinant DNA traits for planting seed products formulate, implement and adhere to strict product stewardship plans. These stewardship plans require the use of validated quantitative and qualitative protein detection methods for various components of the recombinant trait to track trait introgression and seed production activities, as well as monitoring grain harvest. These detection methods must be facile and robust enough to use under GLP and non-GLP conditions. Moreover the methods must be user friendly enough to be easily employed by farmers in the field, grain dealers at the silo, and customs officials at the borders. Therefore, robust, high quality, user friendly protein detection methods and commercial kits are useful and necessary.

While ELISAs are well known in the art, developing robust, high quality, validated ELISA methods that are reproducibly able to detect a particular transgenic product in an array of plant tissue in both lab and field settings is neither trivial nor routine. Still more challenging is to find antibody pairs that are particularly suited to the development of a lateral flow strip and/or ELISA for detecting a functioning PAT transgenic event.

BRIEF SUMMARY OF THE INVENTION

The present invention provides a panel of monoclonal antibodies (mAbs), 155AD4, 155E2.1.114, 155Q3, 155Q12, and 155Q19.1 and the hybridoma cell lines that produce these mAbs. These mAbs are surprisingly well suited for detecting transgenic events that express PAT protein in a variety of plants and plant tissues. The invention further provides quantitative and qualitative immunoassays using the immunoglobulins of the invention and generally includes a method for identifying the presence of a PAT enzyme comprising a) immobilizing a first claimed mAb onto an assay surface then washing said assay surface; b) contacting said assay surface with a liquid suspected of containing PAT for a period of time sufficient to allow binding then washing said assay surface; c) contacting said assay surface with a different claimed second antibody conjugated to a reporting group for a period of time sufficient to allow binding of said second conjugated monoclonal antibody then washing said assay surface; and, d) detecting the presence or absence of said reporting group. The invention further generally includes a method for the quantitative determination of a PAT enzyme comprising a) immobilizing a PAT-specific polyclonal antibody onto an assay surface; b) contacting said assay surface with a liquid suspected of containing PAT for a period of time sufficient to allow binding then washing said assay surface; c) contacting said assay surface with a different claimed second antibody conjugated to a reporting group for a period of time sufficient to allow binding of said second conjugated monoclonal antibody then washing said assay surface; and, d) quantitating the presence of said reporting group by interpolating from comparison to a calibration curve. The invention also includes methods of using the mAbs for isolating or detecting PAT comprising: a) immobilizing said antibody onto a surface; b) contacting said immobilized antibody with a mixture containing PAT; c) separating said immobilized antibody bound to PAT from said mixture; and d) recovering PAT by removing the antibody-bound PAT from said immobilized antibody.

BRIEF DESCRIPTION OF THE DRAWINGS

FIG. 1 is an ELISA standard curve analysis. Purified recombinant PAT protein was diluted to 7 concentrations ranging from 0.25 to 6.0 ng/mL. The concentrations were plotted using optical density readings at 450 nm after subtracting a background OD at 650 nm.

DETAILED DESCRIPTION OF THE INVENTION

The present invention encompasses antibodies that specifically bind PAT and the hybridomas that produce the mAbs. The table below lists the claimed hybridoma cell line designations and their corresponding deposit dates.

| Hybridoma/mAb Designation | ATCC Deposit Designation | ATTC Deposit Date |
| --- | --- | --- |
| 155AD4 | PTA-13188 | 12 Sep. 2012 |
| 155E2.1.114 | PTA-13189 | 12 Sep. 2012 |
| 155Q3 | PTA-13187 | 12 Sep. 2012 |
| 155Q12 | PTA-13190 | 12 Sep. 2012 |
| 155Q19.1 | PTA-13186 | 12 Sep. 2012 |

The hybridoma cell lines were deposited and will be made available to the public without restriction, but subject to patent rights, with the American Type Culture Collection (ATCC), 10801 University Boulevard, Manassas, Va., 20110. The claimed cell lines were deposited on behalf of Dow AgroSciences LLC on Sep. 12, 2012. These deposits were made and will be maintained in accordance with, and under the terms of, the Budapest Treaty with respect to cell line deposits for the purposes of patent procedure. These deposits will be maintained without restriction at the ATCC depository, which is a public depository, for a period of 30 years, or five years after the most recent request, or for the effective life of the patent, whichever is longer, and will be replaced if they become nonviable during that period.

The invention includes methods of using the mAbs for isolating or detecting PAT comprising immobilizing said antibody onto a surface, contacting said immobilized antibody with a mixture containing PAT, separating said immobilized antibody bound to PAT from said mixture and recovering PAT by removing the antibody-bound PAT from said immobilized antibody.

The invention further includes a method of using the claimed antibodies for identifying the presence of PAT in a biological sample comprising immobilizing said antibody onto an assay surface contacting said assay surface with a liquid suspected of containing PAT and washing said assay surface with a suitable solution, contacting said assay surface with an anti-PAT antibody labeled with a reporting group and washing said assay surface with a suitable solution and detecting the presence of said reporting group.

The invention further includes an analytical method for the quantitative determination of PAT enzyme expressed in transgenic plants, especially maize, soybean and cotton plants. The PAT protein is extracted from a plant samples with a phosphate buffered saline solution. The extract is centrifuged and the aqueous supernatant is collected and diluted. An aliquot of the diluted sample is incubated with enzyme-conjugated anti-PAT monoclonal antibody of the claimed invention in the wells of an anti-PAT polyclonal or monoclonal antibody-coated plate in a sandwich ELISA format. Both antibodies in the sandwich pair capture the PAT protein in the sample. At the end of the incubation period, the unbound reagents are removed from the plate by washing with PBST. The presence of PAT is detected by incubating the enzyme conjugate with an enzyme substrate, generating a colored product. Since PAT is bound in the antibody sandwich, the level of color development is proportional to the concentration of PAT in the sample (i.e., lower protein concentrations result in lower color development). The absorbance at 450 nm minus absorbance at a reference wavelength (such as 650 nm) is measured using a plate reader. A calibration curve is estimated from seven standard concentrations using a quadratic regression equation. This PAT ELISA is specific and sensitive enough for the quantitation of PAT in plant tissue sample extracts. In addition the antibodies of the invention may be used to confirm the presence of PAT using a standard western blotting procedure.

The preparation of antibodies against proteins of interest is well known in the art. See Galfre and Milstein, Methods in Enzymology, Vol. 73, Academic Press, New York (1981); James W. Goding, Monoclonal Antibodies: Principles and Practice, Academic Press, Orlando, Fla. (1986); Current Protocols in Molecular Biolopy, F. M. Ausubel, et al. ed., Wiley Interscience, New York, (1987).

To prepare antibodies reactive with a protein of interest, the protein must be first enriched or purified. Relatively crude antigenic preparations of the protein may be used for immunization purposes. However, highly purified protein is required to determine accurately if hybridomas are producing the sought after monoclonal antibodies or to assay the antibody titers of immune serum.

Once the PAT enzyme has been purified, antibodies specific for PAT may be raised by conventional methods that are well known in the art. Repeated injections into an animal host of choice over a period of weeks or months will elicit an immune response and result in significant anti-PAT serum titers. Preferred hosts are mammalian species and more highly preferred species are rabbits, goats, sheep and mice. Blood drawn from such immunized animals may be processed by established methods to obtain antiserum (polyclonal antibodies) reactive with PAT. The antiserum may then be affinity purified by adsorption to PAT according to techniques known in the art. Affinity purified antiserum may be further purified by isolating the immunoglobulin fraction within the antiserum using procedures known in the art. The resulting material will be a heterogeneous population of immunoglobulins reactive with PAT.

Anti-PAT mAbs are readily prepared using purified PAT. Methods for producing mAbs have been practiced for several decades and are well known to those of ordinary skill in the art. Repeated intraperitoneal or subcutaneous injections of PAT in adjuvant will elicit an immune response in most animals, especially mice. Hyperimmunized B-lymphocytes are removed from the animal and fused with a suitable fusion partner cell line capable of being cultured indefinitely. Numerous mammalian cell lines are suitable fusion partners for the production of hybridomas. Many such lines are commercially available from the ATCC and commercial suppliers.

Once fused, the resulting hybridomas are cultured in a selective growth medium for one to two weeks. Two well-known selection systems are available for eliminating unfused myeloma cells or fusions between myeloma cells from the mixed hybridoma culture. The choice of selection system depends on the strain of mouse immunized and myeloma fusion partner used. The AAT selection system, described by Taggart and Samloff, Science 219, 1228 (1982), may be used; however, the HAT (hypoxanthine, aminopterin, thymidine) selection system, described by Littlefield, Science 145, 709 (1964), is preferred because of its compatibility with mouse cells and fusion partners mentioned above.

Spent growth medium is then screened for immunospecific mAb secretion. Enzyme-linked immunosorbant assay procedures are best suited for this purpose; though, radioimmuno assays adapted for large volume screening are also acceptable. Multiple screens designed to consecutively pare down the considerable number of irrelevant or less desired cultures must be performed to isolate the small percentage of mAbs of the instant invention. Cultures that secrete mAbs reactive with PAT may be isotyped using commercially available assays.

Hybridoma cultures that secrete the sought-after anti-PAT mAbs may be sub-cloned several times to establish monoclonality and stability. Well known methods for sub-cloning eukaryotic, non-adherent cell cultures include limiting dilution, soft agarose and fluorescence activated cell sorting techniques. After each subcloning, the resultant cultures must be re-assayed for antibody secretion and isotyped to ensure that a stable antibody-secreting hybridoma cell line has been established.

The claimed anti-PAT antibodies can be immobilized to a surface so that some of the antibody binding site remains exposed and capable of binding PAT. A wide assortment of schemes for immobilizing antibodies has developed over the past few decades. Immobilization can be accomplished by covalently coupling the antibody directly to the desired surface or by bridging the antibody to the surface.

CNBr and carbodiimide coupling of antibodies to polysaccharide based beads such as SEPHAROSE® (Pharmacia, Piscataway, N.J.) are illustrative of direct coupling schemes that are consistent with the invention. Direct couplings generally do not orient the antibodies in any particular fashion; however, some types of direct couplings are able to reproducibly orient the antibody on the immobilizing substance.

Preferred coupling schemes orient the antibody such that its antigen binding regions remain exposed. One such scheme utilizes the natural carbohydrate found on the heavy chains of the antibody. By first oxidizing the carbohydrate moieties to the corresponding aldehydes then reacting the aldehyde with a primary amino group on the surface, it is possible to link the antibody in an advantageous orientation.

Many types of bridges are possible and include small organic linkers, which covalently bind the antibody to the immobilizing substance. Such spacer arms are acceptable and preferably should not interact with proteins once the bridge has been formed.

The above discussion is in no way meant to limit the scope of the invention. Numerous other well-known schemes for linking antibodies to immobilizing substances are consistent with the invention.

It is well known that antibodies labeled with a reporting group can be used to identify the presence of antigens in a variety of milieus. Antibodies labeled with radioisotopes have been used for decades in radioimmuno assays to identify, with great precision and sensitivity, the presence of antigens in a variety of biological fluids. More recently, enzyme labeled antibodies have been used as a substitute for radiolabeled antibodies in the popular ELISA.

Antibodies of the present invention can be bound to an immobilizing substance or assay surface, such as a polystyrene well or particle, and used in immunoassays to determine whether PAT is present in a test sample. In this embodiment of the invention, a sample is contacted with the immunoaffinity surface and allowed to incubate. After a washing step, any PAT that has bound to the immunoaffinity surface is detected by contacting the surface with another antibody of the invention labeled with a reporting group.

The use of lateral flow strips or immunochromatographic strips with the claimed antibodies and assay methods is consistent with the invention. Lateral flow assays are well known in the art. See for example U.S. Pat. No. 6,485,982. In this mode lateral flow tests can be used for qualitative or semi-quantitative detection of PAT alone or simultaneously with other analytes. Lateral flow tests are the simplest to use of all the test formats described herein and are particularly useful in field settings where plant material is quickly extracted into a solution and tested on a lateral flow strip. In this mode it is only necessary to place the lateral flow strip into a liquid sample or to apply the liquid sample to the lateral flow strip and read the results after a predetermined time. All lateral flow tests should incorporate either a procedural control line or a sample control line that is used to validate the test result. Appearance of two lines, therefore, indicates a positive result, while a valid negative test produces only the control line. If only the test line appears, or if no lines appear, it is invalid.

A typical lateral flow test strip consists of four main components; a sample pad upon which the test sample is applied, a conjugate pad that contains antibodies of the present invention conjugated to colored particles (typically colloidal gold particles, or latex microspheres); a reaction membrane, such as a hydrophobic nitrocellulose or cellulose acetate membrane onto which a different antibody of the invention is immobilized in a line across the membrane as a capture zone or test line; a species-specific secondary antibody to capture the non-bound PAT Ab-gold conjugate to form the control line; and, a waste reservoir designed to draw the sample across the reaction membrane by capillary action.

The components of the lateral flow strip are normally fixed to an inert backing material and may be presented in a simple dipstick format or within a plastic casing with a sample port and reaction window showing the capture and control zones. In another mode of the assay embodiment, a test sample suspected of containing PAT is dried onto a surface, forming an immobilized test sample. A labeled antibody of the invention is then contacted with the immobilized test sample and allowed to incubate. If the sample contains PAT, the labeled antibody will bind to the immobilized PAT. This method can also be done using an unlabeled antibody of the invention followed by a labeled secondary antibody that binds to an antibody of the invention which has already bound to PAT. After washing, the immobilized test sample is measured to detect the presence of any reporting groups.

Reporting groups are typically enzymes, such as alkaline phosphatase, horseradish peroxidase or beta-D-galactosidase. Suitable substrates produce a color change when reacted with the enzyme. In so doing, measurements of the color intensity can be quantitated using a spectrophotometer. If the reporting group is a radioisotope, an appropriate gamma or beta ray detecting instrument can be used to quantitate the reporting group. The intensity of the reporting group directly correlates, with the amount of PAT in the test sample.

The following examples will help describe how the invention is practiced and will illustrate the characteristics of the claimed anti-PAT antibodies and assays.

EXAMPLE 1

Monoclonal Antibody Generation

Mice were immunized with purified recombinant PAT protein, and standard, PEG-mediated fusion techniques were used to prepare a panel of hybridomas expressing anti-PAT monoclonal antibodies. Samples of spent tissue culture media were removed aseptically from each well containing a hybridoma culture and assayed for PAT reactivity using the following antibody capture ELISA method. Microtiter wells were coated with a solution of 1-10 µg/mL of purified recombinant PAT protein. The wells were washed and samples of spent tissue media were placed in the wells and allowed to incubate. The wells were washed and horseradish peroxidase-labeled anti-mouse antibody was added and allowed to incubate. The plates were washed, substrate was added to develop a color reaction and the plates were read for optical density (OD). Wells with high OD readings were mapped back to culture wells containing the hybridomas. The PAT antibody positive cultures were continually screened for antibody production to assure growth stability and antibody production as the cultures were expanded. Several rounds of limiting dilution cloning were preformed to establish true monoclonality for each culture. Further assays on antibody positive clones were conducted to determine the suitability of each antibody for use in the presently claimed quantitative detection methods for field use with plant material.

EXAMPLE 2

Immunoblot Assay Development

Western blot conditions were evaluated and established for using either PAT monoclonal or polyclonal antibodies to detection PAT protein from transgenic crop tissue samples. The final assay used SDS-PAGE to separate samples and probed with PAT monoclonal or polyclonal antibodies after blotting to a membrane.

Leaf tissue samples from transgenic soybean expressing PAT were first extracted in a PBST buffer or directly in Laemmli buffer. Then heat-treated samples were subjected to SDS-PAGE. After the proteins were transferred to a PVDF or nitrocellulose membrane, the membrane was blocked in a blocking buffer and then incubated with either PAT monoclonal or polyclonal antibodies at room temperature for approximate 1 hour. After a washing step, the membrane was incubated with an HRP (horseradish peroxidase) conjugated, species-specific secondary antibody (e.g., for PAT monoclonal antibody, the secondary antibody was goat anti-mouse IgG antibody). After incubation, unbound antibodies were washed away and the bound antibodies were incubated with a chemiluminescent substrate. The chemiluminescent signals were captured by exposure to a film at various time intervals to achieve the resulting bands. Both monoclonal and polyclonal antibodies were able to detect PAT protein from transgenic crop tissue samples.

EXAMPLE 3

ELISA Assay Format and Development

Assay conditions were evaluated to determine the optimal antibody pair, antibody coating concentration, coating and blocking buffer constituents, coating format and pH, and antibody-HRP conjugation ratio and concentration. The final assay format used a sequential or simultaneous sandwich format constituting a polyclonal coating antibody and a monoclonal antibody-HRP conjugate.

In this system, PAT polyclonal antibody purified from antiserum lot D2976 was diluted in coating buffer and added to a microtiter plate. After incubation, the wells were blocked with blocking buffer and washed. Purified recombinant PAT protein samples were added to the coated reaction wells and incubated with HRP-conjugated monoclonal antibody 155Q12 for approximately 1 hour. After a washing step, a colorimetric substrate was added to the reaction wells. In the presence of PAT protein, PAT-specific monoclonal antibodies were bound in the reaction wells and the conjugated HRP reacted with HRP and subsequently generated a color change in the wells. After incubation with the substrate for a suitable time, the reactions were stopped by adding a stop solution. The optical densities of the color development were read in a 96-well plate reader at a substrate-specific wavelength (i.e., 450 nm) after substracting reading at a reference wavelength (i.e., 650 nm). The resulting data were plotted and a standard calibration curve was calculated as shown in FIG. 1.

EXAMPLE 4

ELISA Assay Characteristics

A) Standard Calibration Curve Performance:

The assay format was applied for quantitative analysis of PAT proteins extracted from plant materials. The standard calibration curve range was established with seven concentrations ranging from 0.25 to 6.0 ng/mL and the corresponding OD range and variation were evaluated. From five tests performed by various analysts on different days, the results showed the overall standard curve absorbance ranged from 0.113 to 1.773. The precision from the inter-plate and inter-analyst tests resulted in a percent coefficient of variation (CV %) ranging from 8.0% to 12.6% (Table 1a). Using the established calibration curve to back-calculate, predicted standard concentrations showed accurate predication with Mean % Error ranging from 0.4% to 3.5% and variation (CV %) was less 5% from five independent tests (Table 1b).

TABLE 1a

PAT calibration curve performance - OD range and precision

| Sample | Concentration | Mean prediconc | Mean % Error | CV % | (n=) |
|---|---|---|---|---|---|
| Std01 | 6.00 | 5.98 | 0.4 | 0.5 | 5 |
| Std02 | 4.80 | 4.85 | 1.1 | 1.2 | 5 |
| Std03 | 3.60 | 3.55 | 1.4 | 0.7 | 5 |
| Std04 | 2.40 | 2.41 | 1.2 | 1.5 | 5 |
| Std05 | 1.20 | 1.21 | 1.4 | 2.1 | 5 |
| Std06 | 0.60 | 0.60 | 1.6 | 2.0 | 5 |
| Std07 | 0.25 | 0.25 | 3.5 | 4.8 | 5 |

TABLE 1b

PAT calibration curve performance - OD range and precision

| Standard | Conc. (ng/mL) | Test #1 | Test #2 | Test #3 | Test #4 | Test #5 | Average OD | Stdev | CV % | Min OD | Max OD | (n =) |
|---|---|---|---|---|---|---|---|---|---|---|---|---|
| Std01 | 6.00 | 1.669 | 1.680 | 1.428 | 1.715 | 1.773 | 1.653 | 0.132 | 8.0 | 1.428 | 1.773 | 5 |
| Std02 | 4.80 | 1.418 | 1.388 | 1.191 | 1.459 | 1.483 | 1.388 | 0.116 | 8.4 | 1.191 | 1.483 | 5 |
| Std03 | 3.60 | 1.106 | 1.072 | 0.858 | 1.118 | 1.153 | 1.061 | 0.117 | 11.1 | 0.858 | 1.153 | 5 |
| Std04 | 2.40 | 0.811 | 0.748 | 0.598 | 0.793 | 0.84 | 0.758 | 0.095 | 12.6 | 0.598 | 0.840 | 5 |
| Std05 | 1.20 | 0.452 | 0.43 | 0.332 | 0.439 | 0.444 | 0.419 | 0.050 | 11.8 | 0.332 | 0.452 | 5 |
| Std06 | 0.60 | 0.265 | 0.244 | 0.195 | 0.247 | 0.249 | 0.240 | 0.026 | 11.0 | 0.195 | 0.265 | 5 |
| Std07 | 0.25 | 0.149 | 0.137 | 0.113 | 0.148 | 0.137 | 0.137 | 0.014 | 10.6 | 0.113 | 0.149 | 5 |

B) Assay Accuracy:

The assay was evaluated for accuracy by fortifying the negative control crop tissues with known amount of reference standard protein and measuring the recovery. Based on two independent tests, corn and soybean leaf samples were spiked with 0.25 ng/mL (LOD level), 0.60 ng/mL (LOQ level), middle (2.40 ng/mL) and upper levels (6.00 ng/mL) of the quantitative range. The averaged recoveries within the quantitative range (0.60-6.00 ng/mL) were 88.5% and 117% for corn and soybean leaves, respectively, (Table 2), which fell within industry widely practiced 70-120% acceptable range for assay accuracy assessment. The variation from two tests resulted in CV % of 18.3% and 2.5% for corn and soybean, respectively. Different from soybean, corn leaf was out of the 70-120% range at LOD level, but accurate quantitation was not applicable at this level.

TABLE 2

Accuracy assessment for corn and soybean PAT protein quantitation

| Tissue | Spiked Level (ng/mL) | Average Recovery (%) | Stdev | CV % | n |
|---|---|---|---|---|---|
| Corn Leaf | 6.00 | 76.0 | 3.1 | 4.1 | 2 |
|  | 2.40 | 82.6 | 7.8 | 9.4 | 2 |
|  | 0.60 (LOQ) | 106.8 | 17.5 | 16.4 | 2 |
|  | 0.25 (LOD) | 169.8 | 42.3 | 24.9 | 2 |
|  | 0.60-6.00 | 88.5 | 16.2 | 18.3 | 6 |
| Soybean Leaf | 6.00 | 120.3 | 1.8 | 1.5 | 2 |
|  | 2.40 | 116.0 | 5.8 | 5.0 | 2 |
|  | 0.60 (LOQ) | 114.8 | 5.4 | 4.7 | 2 |
|  | 0.25 (LOD) | 119.3 | 0.2 | 0.2 | 2 |
|  | 0.60-6.00 | 117.0 | 2.9 | 2.5 | 6 |

C) Transgenic PAT Protein Quantitation from Crop Tissue Sample:

The assay was applied to crop tissue samples to measure PAT protein expression. As shown in Table 3, one negative control soybean leaf sample and three PAT transgenic soybean leaf samples were analyzed at multiple dilutions by ELISA assay. The linearity and precision were assessed by calculating the CV % from the adjusted result across multiple dilutions and across replicate samples, respectively. Both CV % was less than 5%, indicating good linearity and precision of the assay.

TABLE 3

PAT protein quantitation from soybean leaf samples by ELISA analysis

| Sample | Mean OD | Mean Result (ng/mL) | CV % | Dilution | Adjusted Result (ng/mL) | Average (ng/mL) | CV % |
|---|---|---|---|---|---|---|---|
| Buffer Blank | 0.058 | N.D. | N.A. | 1 | N.D. | N.A. | N.A. |
| Neg Soy (1:1) | 0.073 | N.D. | N.A. | 1 | N.D. | N.D. | N.A |
| Neg Soy (1:2) | 0.073 | N.D. | N.A. | 2 | N.D. |  |  |
| Soy#1 (1:100) | 0.593 | 2.36 | 1.6 | 100 | 235.86 | 232.02 | 2.3 |
| Soy#1 (1:50) | 1.103 | 4.56 | 1.0 | 50 | 228.19 |  |  |
| Soy#2 (1:100) | 0.602 | 2.40 | 1.1 | 100 | 239.69 | 234.07 | 3.4 |
| Soy#2 (1:50) | 1.105 | 4.57 | 1.2 | 50 | 228.45 |  |  |
| Soy#3 (1:100) | 0.597 | 2.38 | 1.5 | 100 | 237.72 | 235.06 | 1.6 |
| Soy#3 (1:50) | 1.123 | 4.65 | 1.3 | 50 | 232.40 |  |  |
|  |  |  |  |  | Overall Mean | 233.72 |  |
|  |  |  |  |  | Stdev | 1.55 |  |
|  |  |  |  |  | CV % | 0.7 |  |
|  |  |  |  |  | n = | 3 |  |

Adjusted Result, Mean Result are from replicate determinations multiplied by the dilution factor;
N.D., not detectable if the Mean OD was less than OD of LOD level on the calibration curve;
N.A., not applicable.

EXAMPLE 5

PAT Quantitative ELISA Protocol

Equipment and Materials

Balance, analytical, Model AE50, Mettler Instrument Corporation, Hightstown, N.J. 08520.

Centrifuge, capable of holding 96-well plates, Model GR422, catalog number 11176916, Jouan, Inc., Winchester, Va. 22602.

Centrifuge, capable of holding 2 mL Eppendorf tubes, Eppendorf-5417C, Brinkmann Instruments. Inc., Westbury, N.Y. 11590.

Freezer, capable of maintaining −20° C., Model 75F, U-Line Corporation, Milwaukee, Wis. 53223.

Freezer, capable of maintaining −80° C., Model ULT2586, catalog number 13-989-233, Fisher Scientific, Pittsburgh, Pa. 15205.

Incubator, Precision, Economy, catalog number 51221087, Jouan, Inc.

Mortar, porcelain, Coors 60316, catalog number 12-961A, Fisher Scientific.

Pestle, porcelain, Coors 60317, catalog number 12-961-5A, Fisher Scientific.

Pipettor, various sizes, Rainin, Woburn, Mass. 01888.

Pipettor, 8- or 12-channel, Rainin, Woburn, Mass. 01888.

Pipet Aid, portable, catalog number 13-681-19, Fisher Scientific.

Plate reader, MAXline® Vmax microplate reader with SOFTMAX PRO® software, capable of reading 450 and 650 nm, catalog number 0200-2018, Molecular Devices, Sunnyvale, Calif. 94089

Refrigerator, capable of maintaining 4° C., catalog number 13-991-86, Fisher Scientific.

Shaker/Grinder, Model Geno/Grinder, catalog number 2000-115, Certiprep, Metuchen, N.J. 08840.

Stir plate, Model 220T, catalog number 14-493-220T, Fisher Scientific.

Vortex, Genie-2 Model, catalog number 12-812, Fisher Scientific.

Washer, 96-well microplate, Model Elx 405, Bio-Tek Instruments, Inc., Winooski, Vt. 05404.

Water purification system, Model Milli-Q UV Plus, Millipore Corporation, Milford, Mass. 01757.

Basin, Reagent, non-sterile, catalog number 13-681-100, Fisher Scientific.

Bead, ⅛" chrome steel, catalog number 039347, Small Parts Inc., Miami Lakes, Fla. 33014-0650.

Pipet, 10-mL disposable serological, catalog number 13-678-11E, Fisher Scientific.

Pipet tip, various sizes, Fisher Scientific.

Plate, 96-well, deep-well polypropylene non-binding for sample dilution, Fisher Scientific.

Plate sealer, 96-well, catalog number 07-200-375, Fisher Scientific.

Tubes, 1.2-mL polypropylene cluster, 96 tubes per rack, catalog number 7200320, Fisher Scientific.

Tube, 2.0-mL conical polypropylene Eppendorf microcentrifuge, catalog number 02-681-344, Fisher Scientific.

Cap, for 2.0-mL conical tube, catalog number 02-681-361, Fisher Scientific.

Tube, 5-mL polypropylene centrifuge with cap, catalog number 14-959-11A, Fisher Scientific.

Tube, 15-mL polypropylene centrifuge with cap, catalog number 05-538-59A, Fisher Scientific.

Tube, 50-mL polypropylene centrifuge with cap, catalog number 05-526B, Fisher Scientific.

Weigh dish, small, catalog number 02-204A, Fisher Scientific.

Reagents and Standards

PAT antibody-coated 96-well microliter plate, PAT antibody conjugate solution, colorimetric substrate solution, stop solution.

PBST, pH 7.4, packets for making 1 L, catalog number P-3563, Sigma. Store at 2-8° C.

Polyvinylpyrrolidone (PVP), molecular weight 40,000, catalog number PVP-40, Sigma.

PAT microbial standard protein.

Wash buffer: PBS, pH 7.4, with 0.05% Tween 20 (PBST)

Assay buffer: Phosphate Buffered Saline, pH 7.4, with 0.05% Tween 20 plus 1% PVP (w/v) (PBST/PVP):

Assay Procedure

Equilibrate PAT ELISA reagents to 20-25° C. by removing from the refrigerator at least 30 minutes prior to performing the assay.

Prepare PAT Working Stock Solution, 100 ng/mL

The starting PAT standard may be lyophilized powder or aliquoted liquid stock solutions. For example, one stock solution is a 0.3 mg/mL solution.

Vortex the stock solution and then add a minimum of 10 µL of the 0.3-mg/mL PAT stock solution into 990 µL of PBST/PVP and mix well to make the 3000-ng/mL stock solution. Similarly, add 40 µL of the 1000-ng/mL stock solution into 1160 µL of PBST/PVP and mix well to make the 100-ng/mL stock solution. Keep them on ice and use within 2 hours. Discard if any visible contamination is observed.

Prepare PAT Calibration Curve Solutions per Table 4.

TABLE 4

| Conc. of Stock Soln. (ng/mL) | Aliquot of Stock Soln (µL) | Starting Buffer Volume (µL) | Final Soln. Volume (µL) | Final Standard Conc. (ng/mL) | Remaining Volume after Aliquot (µL) |
|---|---|---|---|---|---|
| 100 | 105 | 1645 | 1750 | 6.00 | 550 |
| 6.00 | 1200 | 300 | 1500 | 4.80 | 600 |
| 4.80 | 900 | 300 | 1200 | 3.60 | 500 |
| 3.60 | 700 | 350 | 1050 | 2.40 | 600 |
| 2.40 | 450 | 450 | 900 | 1.20 | 500 |
| 1.20 | 400 | 400 | 800 | 0.60 | 550 |
| 0.60 | 250 | 350 | 600 | 0.25 | 600 |
| 0 | 0 | 500 | 500 | 0 | 500 |

Sample Preparation

A) Crop tissue samples are stored frozen at −80° C. until lyophilized. After lyophilization, samples are ground and then stored in a −80° C. freezer until weighed for analysis.

B) Generally, weigh 15-mg portions of the prepared tissue samples and dispense into 2-mL polypropylene tubes. Add two or three metal beads to each tube and 1.5 mL of PBST/PVP assay buffer. A reagent blank and a control should be carried through the method with each sample set. The reagent blank contains 1.5 mL of PBST/PVP assay buffer.

C) Cap all of the tubes. Extract the samples using the Geno/Grinder automatic shaker/grinder at a dial setting of 500 and the toggle switch at the 1× setting (approximately 1500 strokes per minute) for 3 minutes as one cycle.

D) Centrifuge the samples at 3,000 (or greater) rpm for 5 minutes or until separated (no visible particles in the supernatant). The supernatant can be transferred to a separate tube or subject to further dilutions in assay buffer for analysis as described in following steps. Keep the extract on ice and assay it within 4 hours.

Conduct each test on one individual microtiter plate. The average of duplicate analyses of a sample or standard constitutes a single result. A calibration curve and the appropriate control must be included in each plate.

Transfer the ELISA standard calibration solutions to a non-binding 96-well dilution plate and record the location on the 96-well assay template sheet.

Prepare sample dilutions as needed and transfer diluted samples to the non-binding 96-well dilution plate containing the standard calibration solutions and record the location on the 96-well assay template sheet.

Dispense approximate 6 mL of the PAT antibody conjugate per plate into a reagent basin.

Pipet 50 µL of the PAT antibody conjugate from the reagent basin to each well of the antibody coated 96-well microtiter plate. Discard any unused PAT antibody conjugate solution.

Add 100 µL of the ELISA standard solutions and diluted samples from the non-binding 96-well dilution plate to the antibody coated 96-well microtiter plate, keeping the same orientation as the 96-well assay template. Change pipet tips with each sample.

Cover the plate with an adhesive plate sealer. Gently swirl the ELISA plate on the benchtop or on a plate shaker for approximately ten seconds to mix the reference standards and diluted samples with the PAT antibody conjugate.

Shake the microtiter plate at room temperature (20-30° C.) for approximately 60 minutes on a plate shaker.

Wash the plate five times with 350 µL/well PBST using an automatic plate washer. Tap out excess liquid on a paper towel.

Dispense approximately 12 mL of the color reagent (Substrate Solution) per plate into a reagent basin.

Pipet 100 µL of the color reagent from the reagent basin into each well of the antibody coated 96-well microtiter plate. Cover the plate and gently mix. Discard any unused color reagent solution.

Shake the microtiter plate at room temperature (20-30° C.) for approximately 30 minutes on a plate shaker.

Dispense approximately 12 mL per plate of the Stop Solution into a reagent basin.

Add 100 µL of Stop Solution to each well to stop the reaction. Mix the plate gently. The addition of stop solution should be completed without interruption. Protect the microtiter plate from sunlight; otherwise, color intensity is influenced.

Read the absorbance at 450 nm minus 650 nm using a 96-well microtiter plate reader. All readings should be completed within 30 minutes of adding the stop solution.

Data Analysis and Calculations: Calibration Curve

The known concentrations of the standard calibration solutions and their subsequent absorbance (optical density) should be used for calibration curve regression. A quadratic regression model was used in SOFTMAX PRO® software to develop the regression curve and subsequent calculations.

The equation fits the best parabola to the standard curve based on the equation:

$$y = A + Bx + Cx^2$$

Where: y=mean absorbance value (OD) and x=reference standard concentration

Calculation of PAT in Unknown Samples

The SOFTMAX PRO® software or Microsoft Excel can be used to calculate the concentration of PAT in each sample. The absorbance values from each well was used to interpolate concentrations from the calibration curve regression (see equation below) and mean sample result, standard deviation and the percent coefficient of variation were then calculated from results of replicate wells.

$$\text{Interpolated concentration } (ng/\text{mL}) = \frac{-B + \sqrt{B^2 - 4C*(A - OD)}}{2C}$$

The final PAT concentration from each sample was calculated as ng/mg based on the sample weight, assay buffer volume used for extraction and dilution factor applied.

$$PAT \text{ concentration } (ng/\text{mg}) = \frac{InterpolatedConc.(ng/\text{mL}) \times ExtractionVolume(\text{mL})}{SampleWeight(\text{mg}) \times Dilution}$$

Criteria for Acceptance of an Analytical Batch

Each run must meet the accepted criteria in the procedure to be valid as listed below. If the data fail to meet these performance criteria, the analyst should evaluate the results; determine the potential source of the variation, and repeat the analysis if necessary.

TABLE 5

| | |
|---|---|
| Assay Buffer Blank (0 ng/mL standard) | Absorbance (450 nm-650 nm) < 0.120 |
| 6 ng/mL standard | Absorbance (450 nm-650 nm) ≥ 1.000 |
| Calibration curve | $r^2$ (Correlation of determination) ≥ 0.990 |
| All positive reference standard, OD | CV (OD) of triplicates ≤ 15% |
| Unknown or QC samples, solution | CV (OD) of replicates ≤ 20%* |

*Only applicable to sample OD values that are above the OD of LOD level (0.25 ng/mL).

While this invention has been described relative to the specification and Examples, the present invention may be further modified within the spirit and scope of this disclosure. Further, this application is intended to cover such departures from the present disclosure as come within known or customary practice in the art to which this invention pertains.

What is claimed is:

1. A monoclonal antibody that specifically binds to a phosphinothricin-N-acetyl-transferase (PAT) enzyme selected from the group of monoclonal antibodies consisting of 155AD4, 155E2.1.114, 155Q3, 155Q12, and 155Q19.1, deposited with the American Type Culture Collection (ATCC) under Accession Numbers PTA-13188, PTA-13189, PTA-13187, PTA-13190, and PTA-13186 respectively.

2. The monoclonal antibody of claim 1 produced by the hybridoma having a designation of 155AD4, Accession Number PTA-13188.

3. The monoclonal antibody of claim 1 produced by the hybridoma having a designation of 155E2.1.114, Accession Number PTA-13189.

4. The monoclonal antibody of claim 1 produced by the hybridoma having a designation of -155Q3, Accession Number PTA-13187.

5. The monoclonal antibody of claim 1 produced by the hybridoma having a designation of 155Q12, Accession Number PTA-13190.

6. The monoclonal antibody of claim 1 produced by the hybridoma having a designation of 155Q19.1, Accession Number PTA-13186.

7. A hybridoma cell line that produces a monoclonal antibody of claim 1 that is on deposit with the American Type Culture Collection (ATCC) under Accession Numbers selected from the group consisting of PTA-13186, PTA-13187, PTA-13188, PTA-13189, and PTA-13190.

8. The hybridoma of claim 7 deposited under ATCC Accession Number PTA-13186.

9. The hybridoma of claim 7 deposited under ATCC Accession Number PTA-13187.

10. The hybridoma of claim 7 deposited under ATCC Accession Number PTA-13188.

11. The hybridoma of claim 7 deposited under ATCC Accession Number PTA-13189.

12. The hybridoma of claim 7 deposited under ATCC Accession Number PTA-13190.

13. A method of detecting a phosphinothricin-N-acetyl-transferase (PAT) enzyme comprising:
   a) immobilizing a first monoclonal antibody of claim 1 onto an assay surface then washing the assay surface;
   b) contacting the assay surface with a liquid sample suspected of containing PAT for a period of time sufficient to allow binding of the immobilized first monoclonal antibody to PAT in the sample, then washing the assay surface;
   c) contacting the assay surface with a second monoclonal antibody of claim 1, different from and binding to a different epitope than the first monoclonal antibody, conjugated to a reporting group for a period of time sufficient to allow binding of the conjugated second monoclonal antibody to PAT bound to the immobilized first monoclonal antibody, then washing the assay surface; and
   d) detecting presence or absence or amount of the reporting group bound to the assay surface-immobilized PAT as indicative of presence or absence or amount of PAT in the liquid sample.

14. A method for quantitative determination of a phosphinothricin-N-acetyl-transferase (PAT) enzyme comprising:
   a) immobilizing a polyclonal antibody specific for PAT onto an assay surface;
   b) contacting the assay surface with a liquid sample suspected of containing PAT for a period of time sufficient to allow binding of the immobilized polyclonal antibody to PAT in the sample, then washing the assay surface;
   c) contacting the assay surface with the monoclonal antibody of claim 1 conjugated to a reporting group for a period of time sufficient to allow binding of the conjugated monoclonal antibody to PAT bound to the immobilized polyclonal antibody, then washing the assay surface; and
   d) detecting an amount of the reporting group bound to the assay surface-immobilized PAT as indicative of an amount of PAT in the liquid sample.

15. The method of claim 14 wherein the conjugated monoclonal antibody is selected from the group consisting of 155Q12 and 15Q19.1, Accession Numbers PTA-13190, and PTA-13186 respectively.

16. The method of claim 14 wherein the conjugated monoclonal antibody is 155Q12, Accession Number PTA-13190.

17. The method of claim 14 wherein the conjugated monoclonal antibody is 155Q19.1, Accession Number PTA-13186.

* * * * *